US00PP20897P2

(12) United States Plant Patent
Miyazaki

(10) Patent No.: US PP20,897 P2
(45) Date of Patent: Mar. 30, 2010

(54) ***PHLOX* PLANT NAMED 'SUNPHLOCONSA'**

(50) Latin Name: *Phlox drummondii*
Varietal Denomination: Sunphloconsa

(75) Inventor: Kiyoshi Miyazaki, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/284,879

(22) Filed: Sep. 22, 2008

(51) Int. Cl.
*A01H 5/00* (2006.01)

(52) U.S. Cl. ..... Plt./320

(58) Field of Classification Search ..... Plt./320
See application file for complete search history.

(56) References Cited

U.S. PATENT DOCUMENTS

PP16,361 P2 * 3/2006 Miyazaki ..... Plt./320

OTHER PUBLICATIONS

Telly's Spring 2009 Planting guide, available at: http://www.tellys.com/system/files/2009Tellys_SpringGuidePDF.pdf.*
UPOV ROM GTITM Computer Database, GTI Jouve Retrieval Software 2009/03 Citation for 'Sunphloconsa'.*

* cited by examiner

*Primary Examiner*—Wendy C Haas
(74) *Attorney, Agent, or Firm*—C. A. Whealy

(57) ABSTRACT

A new and distinct cultivar of *Phlox* plant named 'Sunphloconsa', characterized by its compact and mounding plant habit; freely branching and flowering habit; long flowering period; salmon pink-colored flowers; and good garden performance.

1 Drawing Sheet

Botanical designation: *Phlox drummondii.*

Cultivar denomination: 'Sunphloconsa'.

BACKGROUND OF THE INVENTION

The present invention relates to a new and distinct cultivar of *Phlox*, botanically known as *Phlox drummondii* and hereinafter referred to by the name 'Sunphloconsa'.

The new *Phlox* plant is a product of a planned breeding program conducted by the Inventor in Higashiomi, Shiga, Japan. The objective of the breeding program is to create new compact and mounding *Phlox* cultivars with freely branching habit, attractive flower coloration and tolerance to high temperatures.

The new *Phlox* plant originated from a cross-pollination made by the Inventor in Higashiomi, Shiga, Japan in June, 2004, of a proprietary selection of *Phlox drummondii* identified as code number 3Ph-24a, not patented, as the female, or seed parent with a proprietary selection of *Phlox drummondii* identified as code number 4Ph-19, not patented, as the male, or pollen, parent. The new *Phlox* was discovered and selected by the Inventor as a single flowering plant from within the progeny of the stated cross-pollination in a controlled greenhouse environment in Higashiomi, Shiga, Japan in 2005.

Asexual reproduction of the new *Phlox* plant by cuttings in a controlled greenhouse environment in Higashiomi, Shiga, Japan since August 2005, has shown that the unique features of this new *Phlox* plant are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunphloconsa'. These characteristics in combination distinguish 'Sunphloconsa' as a new and distinct cultivar of *Phlox:*

1. Compact and mounding plant habit.
2. Freely branching and flowering habit.
3. Long flowering period.
4. Salmon pink-colored flowers.
5. Good garden performance.

Plants of the new *Phlox* differ from plants of the female parent selection in the following characteristics:

1. Plants of the new *Phlox* have larger flowers than plants of the female parent selection.
2. Plants of the new *Phlox* and the female parent selection differ in flower color as plants of the female parent selection have light pink-colored flowers.

Plants of the new *Phlox* differ primarily from plants of the male parent selection in plant size as plants of the new *Phlox* are larger than plants of the male parent selection.

Plants of the new *Phlox* can also be compared to plants of *Phlox drummondii* 'Sunphlopin', disclosed in U.S. Plant Pat. No. 16,361. In side-by-side comparisons conducted in Higashiomi, Shiga, Japan, plants of the new *Phlox* and 'Sunphlopin' differed in the following characteristics:

1. Plants of the new *Phlox* were not as broad as plants of 'Sunphlopin'.
2. Plants of the new *Phlox* had shorter internodes than plants of 'Sunphlopin'.
3. Plants of the new *Phlox* had larger leaves and flowers than plants of 'Sunphlopin'.
4. Plants of the new *Phlox* and 'Sunphlopin' differed in flower color as plants of 'Sunphlopin' have red purple-colored flowers.

BRIEF DESCRIPTION OF THE PHOTOGRAPHS

The accompanying colored photographs illustrate the overall appearance of the new *Phlox*, showing the colors as true as it is reasonably possible to obtain in colored reproductions of this type. Colors in the photographs may differ slightly from the color values cited in the detailed botanical description which accurately describe the colors of the new *Phlox*.

The photograph at the top of the sheet comprises a side perspective view of a typical flowering plant of 'Sunphloconsa' grown in a container.

The photograph at the bottom of the sheet is a close-up view of typical flowers of 'Sunphloconsa'.

DETAILED BOTANICAL DESCRIPTION

The aforementioned photographs and following observations, measurements and values describe plants grown in Higashiomi, Shiga, Japan, under commercial practice during the late spring and early summer in an outdoor nursery with day temperatures averaging 25° C. and night temperatures averaging 15° C. Plants had been growing for seven months when the photographs and description were taken. In the following description, color references are made to The Royal Horticultural Society Colour Chart, 2001 Edition, except where general terms of ordinary dictionary significance are used.

Botanical classification: *Phlox drummondii* 'Sunphloconsa'.

Parentage:

*Female, or seed, parent*.—Proprietary selection of *Phlox drummondii* identified as code number 3Ph-24a, not patented.

*Male, or pollen, parent*.—Proprietary selection of *Phlox drummondii* identified as code number 4Ph-19, not patented.

Propagation:

*Type*.—By cuttings.

*Time to initiate roots*.—About two to three weeks at 20° C. to 25° C.

*Time to produce a rooted young plant*.—About one to two months at 20° C. to 25° C.

*Root description*.—Fibrous; white in color.

*Rooting habit*.—Freely branching; moderately dense.

Plant description:

*Plant form/habit*.—Compact and mounding plant habit; vigorous growth habit. Freely branching habit with lateral branches potentially developing at every node; pinching enhances branching.

*Plant height*.—About 21.6 cm.

*Plant width (spread)*.—About 26 cm.

*Lateral branches*.—Length: About 10.8 cm. Diameter: About 2.3 mm. Internode length: About 7 mm. Strength: Strong. Texture: Pubescent. Color: Close to 144B.

Foliage description:

*Arrangement*.—Alternate, simple; sessile.

*Length*.—About 4.3 cm.

*Width*.—About 1.5 cm.

*Shape*.—Narrowly elliptic.

*Apex*.—Acute.

*Base*.—Truncate to cordate.

*Margin*.—Entire.

*Texture, upper and lower surfaces*.—Pubescent.

*Venation pattern*.—Pinnate, reticulate.

*Color*.—Developing and fully expanded leaves, upper surface: Close to 144A; venation, close to 145C. Developing and fully expanded leaves, lower surface: Close to 147B; venation, close to 145C.

Flower description:

*Flower type/habit*.—Single rotate flowers arranged in terminal and axillary cymes; flowers face mostly upright or outwardly. Cymes roughly hemispherical in shape. Freely flowering habit with about three to four open flowers per inflorescence.

*Fragrance*.—Moderately fragrant; sweet and pleasant.

*Natural flowering season*.—Continuously flowering from spring to autumn in Japan.

*Postproduction longevity*.—Flowers last about five days on the plant; flowers not persistent.

*Flower buds*.—Height: About 2.1 cm. Diameter: About 3.5 mm. Shape: Clavate. Color: Close to 38D.

*Inflorescence height*.—About 2.8 cm.

*Inflorescence diameter*.—About 5.4 cm.

*Flower diameter*.—About 3.2 cm.

*Flower depth*.—About 1.4 cm.

*Tube length*.—About 1.4 cm.

*Tube diameter, base*.—About 2.2 mm.

*Petals*.—Quantity per flower: Typically five in a single whorl; petals fused at the base into a narrow tube. Length: About 1.5 cm. Lobe width: About 1.4 cm. Shape: Broadly rhombic. Apex: Acute. Margin: Entire. Texture, upper and lower surfaces and throat: Smooth, glabrous. Texture, tube: Pubescent. Color: Developing petals, upper surface: Close to 48C; towards the base, close to 50B. Developing petals, lower surface: Close to 56B. Fully expanded petals, upper surface: Close to 48D; towards the base, close to 51B. Fully expanded petals, lower surface: Close to 56B. Throat: Close to 18D. Tube: Close to 150D.

*Sepals*.—Quantity per flower: Typically five in a single whorl, fused towards the base; calyx star-shaped. Length: About 6.9 mm. Width: About 1.3 mm. Shape: Lanceolate. Apex: Acute. Margin: Entire. Texture, upper and lower surfaces: Smooth, glabrous. Color, developing and fully expanded sepals, upper surface: Close to 137C. Color, developing and fully expanded sepals, lower surface: Close to 137C.

*Peduncles*.—Length: About 2 mm to 7 mm. Diameter: About 1 mm. Strength: Strong. Texture: Pubescent. Color: Close to 145B.

*Pedicels*.—Length: About 1 mm to 5 mm. Diameter: About 0.5 mm. Strength: Strong. Texture: Pubescent. Color: Close to 145B.

*Reproductive organs*.—Stamens: Quantity per flower: Typically five. Stamen length: About 5 mm to 10 mm. Anther shape: Narrowly oblong. Anther size: About 2.3 mm by 0.5 mm. Anther color: Close to 12B. Pollen amount: Moderate. Pollen color: Close to 12A. Pistils: Quantity per flower: One. Pistil length: About 4.6 mm. Stigma shape: Three-parted. Stigma color: Close to 2B. Style color: Close to 149B. Ovary color: Close to 143C.

*Seed/fruit*.—Seed and fruit development have not been observed.

Disease/pest resistance: Plants of the *Phlox* have not been observed to be resistant to pathogens and pests common to *Phlox*.

Garden performance: Plants of the new *Phlox* have been observed to have good garden performance and tolerate rain, wind and temperatures ranging from about 0° C. to about 35° C.

It is claimed:

1. A new and distinct *Phlox* plant named 'Sunphloconsa' as illustrated and described.

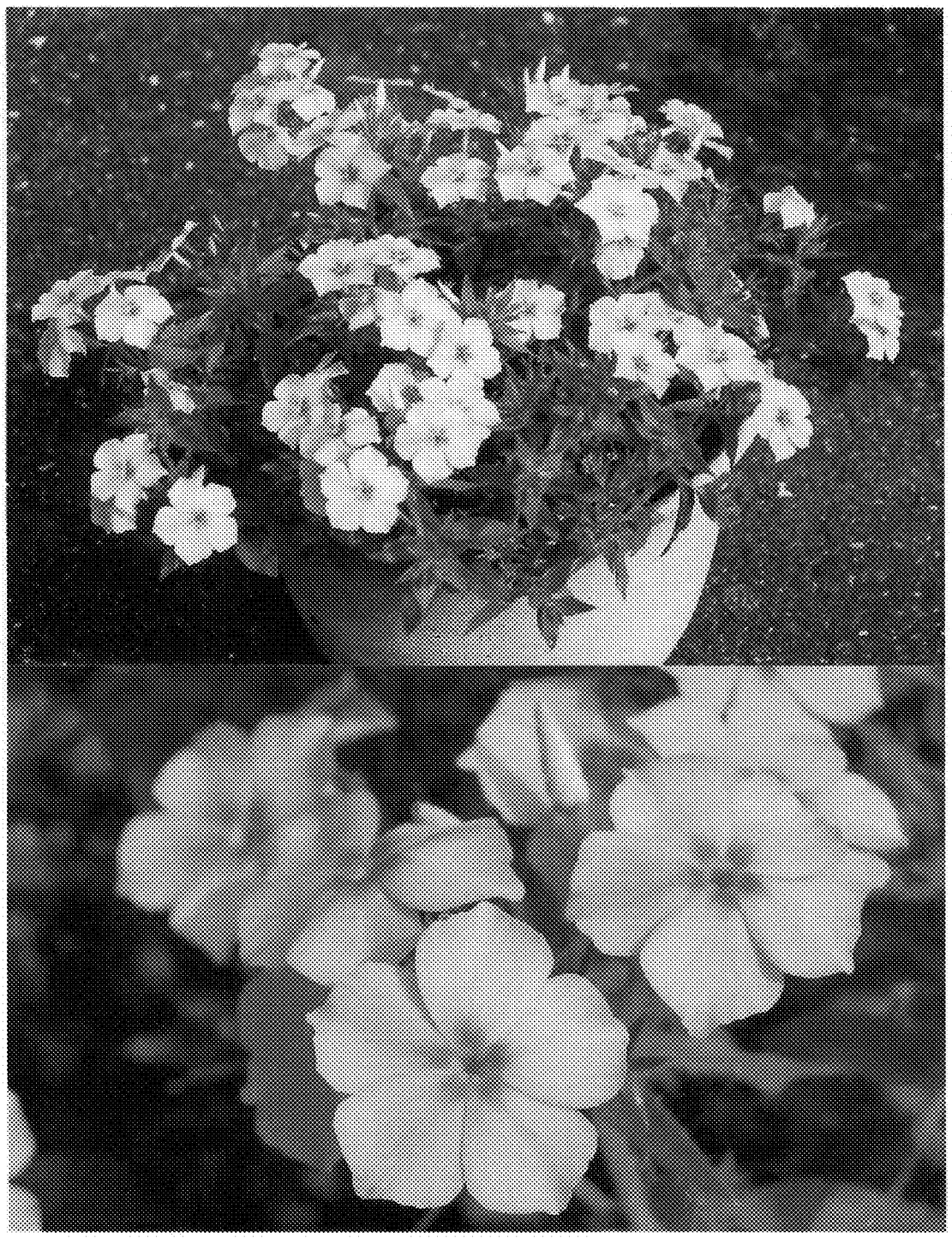

* * * * *